United States Patent [19]
Mirowski et al.

[11] 3,952,750
[45] Apr. 27, 1976

[54] COMMAND ATRIAL CARDIOVERTING DEVICE

[75] Inventors: Mieczyslaw Mirowski, Owings Mills; Morton M. Mower, Baltimore, both of Md.; Aloîs A. Langer, Pittsburgh, Pa.

[73] Assignee: Mieczyslaw Mirowski, Owings Mills, Md.

[22] Filed: Apr. 25, 1974

[21] Appl. No.: 464,180

[52] U.S. Cl. .............................................. 128/419 D
[51] Int. Cl.² ......................................... A61N 1/36
[58] Field of Search ............. 128/419 D, 419 E, 423, 128/422, 419 P

[56] References Cited
UNITED STATES PATENTS

| | | | |
|---|---|---|---|
| 3,258,013 | 6/1966 | Druz | 128/419 D |
| 3,311,111 | 3/1967 | Bowers | 128/422 |
| 3,614,954 | 10/1971 | Mirowski et al. | 128/419 D |
| 3,662,758 | 5/1972 | Glover | 128/419 E |
| 3,727,616 | 4/1973 | Lenzkes | 128/422 |
| 3,738,370 | 6/1973 | Charms | 128/419 D |
| 3,747,605 | 7/1973 | Cook | 128/419 D |
| 3,782,389 | 1/1974 | Bell | 128/419 D |
| 3,798,542 | 3/1974 | Dempsey | 128/419 P |
| 3,805,795 | 4/1974 | Denniston et al. | 128/419 D |

OTHER PUBLICATIONS

Schuder et al., Transactions of the American Society for Artificial Internal Organs, Vol. XVI, 1970, pp. 207–212.

*Primary Examiner*—William E. Kamm
*Attorney, Agent, or Firm*—Fleit & Jacobson

[57] ABSTRACT

An externally controlled implantable electronic device for delivering a cardioverting pulse of energy to the atrium of an ailing heart. In one embodiment, the device is particularly suited for use when the patient visits the office of his physician, and contemplates the transmission of both information and powering energy through the skin of the patient. In another embodiment, the device can be readily operated at home, by the patient, and without the intervention of the physician. Here, the source of energy is permanently implanted.

30 Claims, 3 Drawing Figures

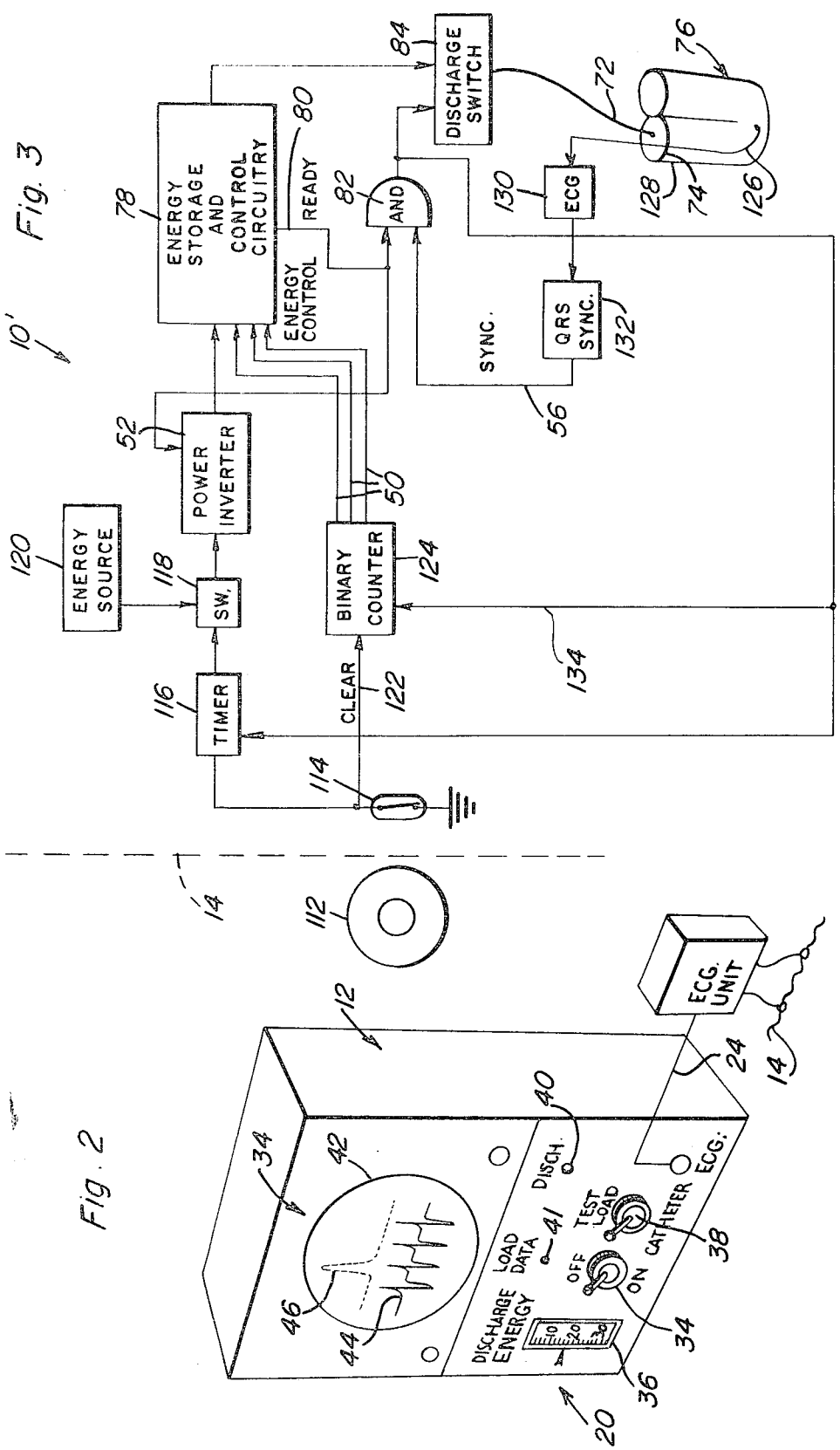

COMMAND ATRIAL CARDIOVERTING DEVICE

BACKGROUND OF THE INVENTION

There are scores of individuals walking the streets today who experience recurring episodes of atrial fibrillation, atrial flutter, or tachycardia. While not life-threatening, these supra-ventricular arrhythmias can become debiliting and lead to complications, and hence require treatment when present. Such individuals require frequent electrical or pharmacological conversion under the care of their physicians to return their hearts to normal sinus rhythm.

Drug therapy is not infrequently successful in correcting atrial fibrillation, flutter or tachycardia, but there are many patients who are resistant to the appropriate drugs or who suffer serious side-effects from the drugs. For these patients, cardioversion is accomplished by way of a technique in which a pulse generator and external paddles combine to send high energy electrical pulses through the ailing patient's thorax to the heart.

For those who suffer from recurring bouts of atrial tachyarrythmias, regular and often times frequent visits to hospitals are in order. Those whose hearts can be successfully returned to normal sinus rhythm by way of drug therapy frequently undergo hospitalization so that the effects of the administered drugs can be carefully monitored. Similarly, those requiring electrical cardioversion are generally cardioverted in the hospital due to the fact that the procedure frequently requires the application of a general anesthetic and carries with it a significant risk to the patient.

It is toward the facilitation of treatment for and the reduction of the risks to those patients suffering from recurring episodes of atrial fibrillation, flutter and tachycardia, that the present invention is directed.

SUMMARY OF THE INVENTION

The present invention relates to an atrial device designed to be implanted under the skin of patients who frequently suffer from bouts of atrial fibrillation, flutter or tachycardia. During those times when the patient is suffering such an arrhythmia, and cardioversion is in order, a command given by the patient or his physician brings the inventive device out of its standby condition to adminsiter a low-level pulse of energy directly to the heart, for example, through a catheter implanted in or about the atrium. Cardioversion by means of an electrical discharge delivered through an intra-atrial catheter has been shown to require energies of five watt-seconds or less, and is thus a painless procedure not requiring anesthesia.

In one embodiment of the present invention, the patient will likely visit the office of his physician for treatment. By way of an external console, the physician programs the desired level of cardioverting energy to be administered. Then, both the power to an implanted discharge capacitor and a set of control signals corresponding to the programmed level of cardioverting energy is transmitted through the skin of the patient and into the implanted unit. In addition, the invention contemplates that an ECG synchronization signal be derived either internally or from an external ECG unit and fed back through the skin of the patient as a command signal to ensure that cardioversion occurs in proper synchronization with the QRS complex. With the present invention, provision can be made to discharge the stored energy through a test load for verifying the readiness of the implanted unit, and information can be extracted through the skin of the patient so that the physician is able to monitor the discharge of the implanted capacitor, which is either through the test load or the implanted atrial catheter.

In another embodiment of the present invention, the patient is able to cardiovert himself at home, without the intervention of his physician. The patient who frequently undergoes attacks of atrial fibrillation, flutter or tachycardia can be taught to recognize the symptoms of such arrhythmias. Once able to recognize that he or she is experiencing such an attack of a convertible arrhythmia, the patient can effect cardioversion when appropriate.

In the second patient-operated embodiment of the present invention, an energy source is incorporated into the implanted cardioverting device. The energy source is normally maintained out of the cardioverting circuit, and is connected into the circuit only upon the issuance of an appropriate command. As here disclosed, the patient issues this command by holding a magnet at an appropriate location against his skin, and a reed switch closes. Upon the closing of the reed switch, the energy source is brought into the circuit, and the discharge cycle is initiated.

In the embodiment of the present invention designed for operation by a physician, the level of cardioverting energy to be delivered to the patient can be manually programmed. In the embodiment of the invention designed for operation without the intervention of a physician, it is also possible to deliver the cardioverting shocks in varied energy levels. In this regard, the patient-operated embodiment of the invention comtemplates sequentially increasing the cardioverting energy level over prior attempts at cardioversion. Specifically, the first attempted cardioversion can be at a relatively low energy level. Then, if unsuccessful, a higher energy can be applied, and so forth. As disclosed, the patient controls repeated discharges by way of the duration of magnet placement against his skin. If low-energy cardioversion is attained, the patient merely removes the magnet from the location of the reed switch. If cardioversion is unsuccessful, the magnet is maintained in position, and the implanted circuitry automatically increases the energy level for the next attempted cardioversion.

Like the first, the second embodiment of the present invention can be equipped with circuitry for synchronizing the cardioverting shocks with the QRS complex. This can be accomplished by way of a sensing probe positioned in or about the heart.

Accordingly, it is one object of the present invention to provide a device which will enable the cardioversion of a heart undergoing atrial fibrillation, flutter or tachycardia, without hospitalization.

Another object of the present invention is to provide a device which will so cardiovert an ailing heart, comfortably and without the administration of an anesthetic.

A further object of the present invention is to provide an implanted device which remains in its standby state until commanded from external to the skin.

Yet another object of the present invention is to provide such an implanted device which receives both command signals and powering energy from external to the skin.

Still a further object of the present invention is to provide a device which will enable the cardioversion of a heart undergoing atrial fibrillation, flutter or tachycardia, without the intervention of a physician.

Additional objects of the present invention are to provide an implanted device whose operation is capable of being verified before discharge into the heart, whose discharge is capable of being synchronized with the QRS complex, in which the energy level of the discharge can be manually programmed or automatically increased in successive attempts at cardioversion, and whose discharges can be monitored from external to the skin of the patient.

These and other objects of the present invention, as well as many of the attendant advantages thereof, will become more readily apparent when reference is made to the following description taken in conjunction with the accompanying drawings.

BRIEF DESCRIPTION OF THE DRAWINGS

FIG. 2 pictorially depicts the physician's console which is represented in FIG. 1 as associating with the inventive implantable device; and FIG. 3 is a block diagram of another embodiment of the inventive implantable command device, suitable for operation without the intervention of a physician.

DETAILED DESCRIPTION OF THE DRAWINGS

Figure 1:
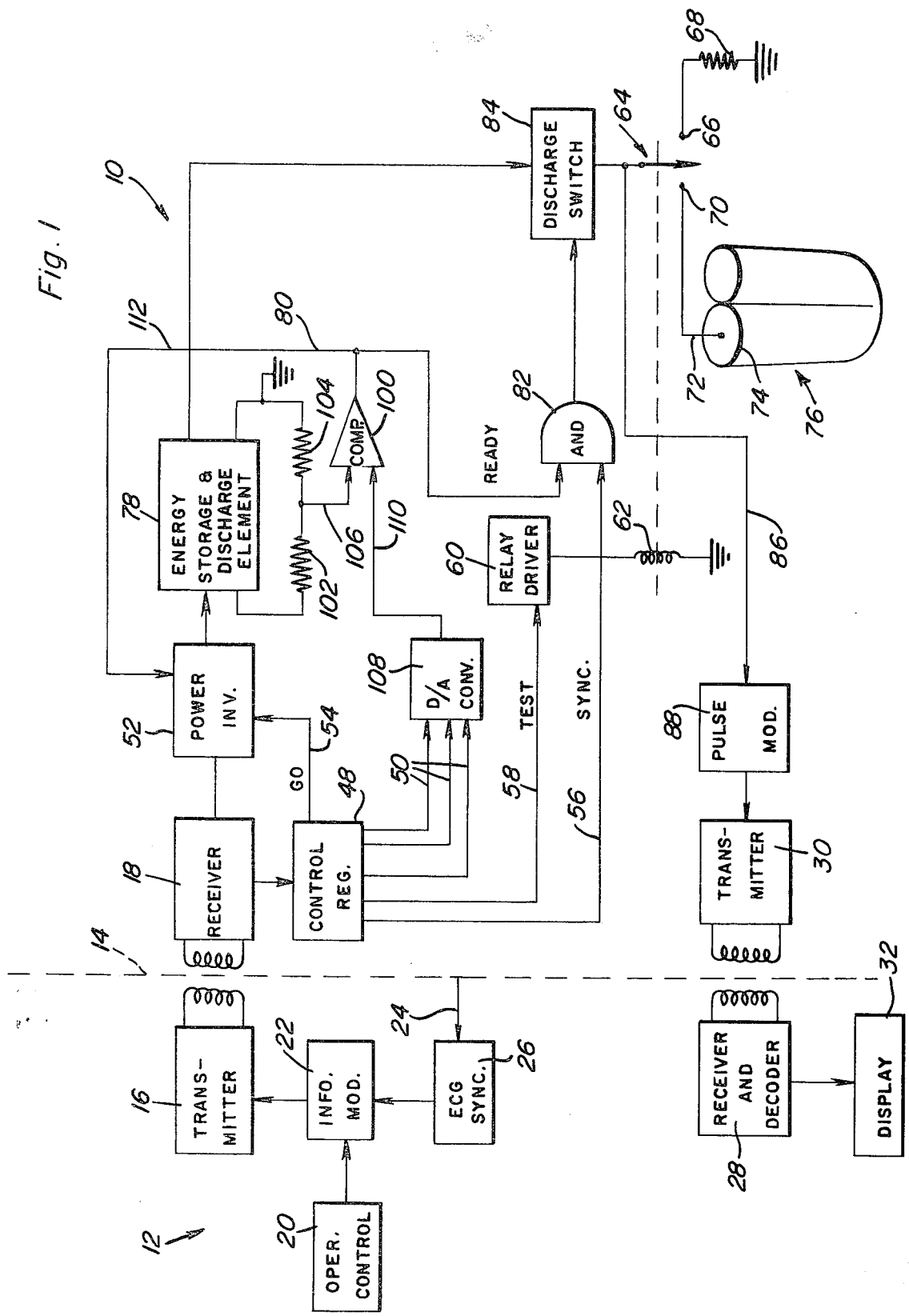
FIG. 1 is a block diagram of an embodiment of the inventive implantable command device particularly suited for use in the office of a physician.

With reference initially to FIGS. 1 and 2, the first embodiment of the present invention will be described. The inventive implantable command device is indicated generally at 10 and is adapted to associate with an external console generally designated at 12. Console 12 includes circuitry for transmitting power and control information to the implanted device for receiving information about the nature of the cardioverting pulses from implanted device as well as signals from other cardiac equipment, and for visually displaying selected cardiac information. The numeral 14 schematically represents the skin of the patient, and hence shows the separation between the implanted device 10 and the external console 12.

The console 12 comprises a power and information transmitter 16 which communicates with an implanted receiver unit 18. Information such as the desired cardioverting energy, whether the unit should be in its "test" or its operating mode, etc., all of which will be explained below, is programmed into an operating control unit 20. Unit 20 may, for example, include a plurality of on-off switches which generate digital signals. The digital signals from operating control unit 20 are fed in parallel to an information modulator circuit 22 where they are converted into a serial chain of operating commands.

Schematically illustrated in FIG. 1 at 24 is an ECG input which may be in the form of a conventional ECG unit or an amplifier which is made an integral part of the console 12. A sequence of electrocardiogram signals taken from the skin 14 of the patient is further illustrated at 44 in FIG. 2. From the electrocardiograph input 24 can be derived impulses which are representative of the occurrence of the QRS complex. The QRS impulses are fed to the information modulator 22 as is schematically represented, from the ECG synchronization unit 26.

Also part of the external console 12 is a receiver and decoder 28 which is adapted to receive and decode information transmitted by the implanted transmitter 30. After being decoded, the information delivered across the skin 14 by transmitter 30 is displayed at an external display unit 32. As can be seen, the implanted transmitter 30 sends signals across the skin 14 of the patient to the receiver and decoder 28 much the same as external transmitter 16 sends signals to implanted receiver 18. Of course, the particular form of modulation could be different.

As represented in FIG. 1, power and information signals are transmitted through the skin of the patient by way of coupled transformer primary and secondary windings. In the specific physician-controlled embodiment herein illustrated and described, power to the implanted unit and the control information is, for simplicity, transmitted along the same channel. The control information can be modulated into the power channel by frequency shift keying, pulse width modulation, or any other appropriate well-known modulation technique. With specific reference to FIG. 2, the external console 12 can be seen to include a display portion 32 and an operating control panel generally designated at 20. Control panel 20 is equipped with an on/off switch 34, an input for the ECG signals 24, a rotary energy discharge dial 36 to enable the physician to control the amount of energy discharged into the heart, a toggle switch 38 for controlling whether the stored energy is discharged into a test load or into the heart, a push button 40 to initiate the discharge of the implanted storage capacitor, and a load-data push button 41. Also illustrated as part of the display portion of external console 12 is a cathode ray tube 42 shown as simultaneously displaying the periodic QRS complex 44 and, in broken lines, the discharge of the implanted storage capacitor.

With continuing reference to FIGS. 1 and 2, the operation of the external unit will be described. The patient suffering from a convertable atrial arrythmia, such as atrial fibrillation, flutter or tachycardia, is examined by the physician, preferably with the aid of ECG equipment. Based upon this input, the physician makes his best estimate of the energy level which will be required to cardiovert the malfunctioning heart, and sets rotary dial 36 accordingly. The ECG synchronization input is then connected to the console 12, the toggle switch 38 is set to either the test load or catheter discharge position, and toggle 34 is moved to the "on" position. At this time, the unit is functional, with energy being transmitted to the implanted circuitry, and with ECG signals being displayed on the display device 32 as shown at 44. The physician then presses the load-date button 41 to transmit the instructions regarding the level of the discharge pulse to the implanted unit at which time the energy storage capacitor is charged to the desired level. When ready, the "discharge" button 40 is depressed, and either the test load or the heart is shocked at the proper time during the QRS complex. The test load is, of course, intended to verify attaining the proper level of discharge before a shock is actually applied to the heart. When the discharge level is verified, the physician simply moves switch 38 to the catheter position, presses the load-data button and then the "discharge" button 40 to deliver a pulse to the heart. Once a shock is actually applied to the heart, the physician observes the screen of CRT 42, and either concludes his activity if cardioversion is successful, or repeats the cardioverting attempt at perhaps a higher energy level if unsuccessful.

When the rotary energy dial 38 and the other controls on panel 20 are set by the physician, the operating control unit 20 provides, for example, a binary signal representative of the energy level to which the dial 36 is set and other operating parameters. This signal takes the form of a parallel binary control word. As noted above, the rotary dial 36 could be replaced by a set of toggle switches, each one of which would provide a discrete binary control signal. The parallel binary control word from the operating control unit 20, as illustrated in FIG. 1, is delivered to the information modulator 22 where it is converted into a serial binary control word. From modulator 22, the serial control word is delivered to the transmitter 16 and sent to the implanted device along the information channel. Simultaneously, the ECG synchronization signal is delivered to the modulator 22.

When the on/off switch 34 on the external console 12 is in the "on" position, the transmitter 16 is activated, and energy in the form of power signals is transformer coupled across the skin of the patient. This energy is received through the secondary winding of the coupling transformer at receiver 18. Then, when the load-data button 41 is depressed, the serial binary control word is transmitted along the information channel. The serial control word recovered by the receiver 18 takes the form of a timed set of pulses. The receiver 18 directs these serial pulses to a control register 48 which reconstructs them into their original parallel format. The parallel control word, along with other control information, provides a signal proportional to the desired energy level which is then transmitted via discrete lines 50 to circuitry associated with a power inverter 52.

Before the activity of the power inverter 52 is initiated, the control register 48 issues a "go" signal which confirms receipt of the control word from the receiver 18. This may be accomplished in any of several well-known ways, for example, by ending each control word with a unique character to designate its end. This "go" command is indicated at 54. As represented in FIG. 1, with three energy control lines 50, a maximum of eight power levels can be set, as a binary format is used. The specific operation of the power inverter 52 and the associated circuitry which serves the purpose of charging the storage capacitor at a predetermined energy level, will be explained below.

The receiver 18 also feeds to the control register 48, information related to the QRS synchronization and whether the energy storage device is to be discharged into the implanted catheter or into a test load. As seen in FIG. 1, the synchronization signal is carried along lead 56 while the test-mode signal is directed along lead 58. The signal on line 58 is fed to a relay driver 60 which associates with coil 62 and in turn, a switch 64. In one position of the switch 64, indicated at 66, energy is directed into a test load 68. In the other position, designated 70, the discharge capacitor feeds directly to a catheter 72 implanted in or about the atrium 74 of a heart 76.

When activated, the power inverter 52 directs energy to an energy storage and discharge device 78 which in this case takes the form of a storage capacitor. When the energy stored by the capacitor 78 reaches the level set on the rotary dial 36, as will be fully explained below, a "ready" signal is produced by a comparator 100 and fed via line 80 to an AND gate 82. The same "ready" signal is also fed back to the power inverter 52.

The "ready" signal which is produced by the comparator 100 is indicative of the discharge capacitor being in readiness for firing through a discharge switch 84. Synchronization signals are, at this time, fed to the AND gate 82 along with the "ready" signal on line 80, and upon the simultaneous occurence of a "ready" signal on line 80 and a QRS synchronization pulse on line 56, AND gate 82 responds by issuing a signal which controls the state of switch 84, and firing the capacitor 78 through the discharge switch. The position of switch 64 determines whether the capicator 78 fires through the test load 68 or through the catheter 72.

The capacitor 78 is charged as explained below. When the control register 48 produces the "go" signal at line 54, this signal reaches a gate input of the power inverter 52. Power inverter 52 can be of any conventional inverter design which produces an output somewhere on the order of 600 volts and can be gated "on" and "off" by the application of external gating commands. The "go" signal from the control register 48 gates the power inverter 52 on, and the relatively constant 600 volt output is thereby initiated. The output of the power inverter 52 is fed directly to the capacitor 78.

As can be seen, a resistive divider in the form of a pair of resistors 102 and 104 is connected across capacitor 78, and the signal appearing at the junction between the registers 102 and 104 is tapped into one point terminal 106 of caparator 100. The "energy control" command which is produced at the control register 48 and fed along lines 50 forms the input to a digital-to-analog converter 108. The converter 108 is of conventional design, with its analog output being directed to the other input terminal 110 of comparator 100.

When the voltage across capacitor 78 reaches the preset desired level, the signal reaching the input 106 of comparator 100 balances the control signal at input 110. At this time, the comparator 100 produces a "ready" signal which is simultaneously transmitted to AND gate 82 along line 80 and to power inverter 52 along feedback path 112. The "ready" signal on line 112 gates the power inverter 52 into its off state. At this point in time, the capacitor 78 is fully and in readiness for discharging into either the test load or the heart, and hence the charging operation is completed.

As noted previously, the present invention contemplates an implanted transmitter 30 associated with the receiver and decoder 28 forming a part of the external console 12. The discharge of the capacitor 78 through either the test load 68 or the catheter 72 is monitored at line 86 which directs a pulse representative of the discharge to a pulse modulator 88. The pulse modulator feeds a modulated signal to transmitter 30 which, in turn, transformer couples the signal across the skin 14 of the patient and to the external receiver and decoder 28. After decoding, the signal representative of the delivery of an electrical shock is displayed on the CRT as at 46 in FIG. 2.

Now, with reference to FIG. 3, the totally implantable embodiment of the inventive atrial device will be described. For convenience of description, those elements which have previously been described with reference to FIG. 1 are similarly numbered in FIG. 3, and will not again be described in detail.

In the embodiment in FIG. 3, each element of the inventive device is implanted beneath the skin 14 of the patient with the exception of a command magnet 112. Here, the patient controls the operation of the implanted device by positioning the command magnet 112 at a location on his body immediately opposite an implanted reed switch 114. When so positioned, reed switch 114 closes, and the implanted device is actuated.

The fully implanted device is generally shown in FIG. 3 at 10'. After the reed switch 114 closes, a timer 116 is turned on and, after a preset delay set into the timer, a switch 118 is closed to direct energy from an implanted battery 120 to the input of the power inverter 52. Simultaneous with the closing of the reed switch 114, a "clear" signal is issued along line 122 and is fed to a binary counter 124 to reset the same to its initial state. It should of course be appreciated that closure of the reed switch 114 also delivers operating power to the timer 116 and to the binary counter 124, but such connections have been eliminated to simplify the block diagram of FIG. 3.

As is evident from FIG. 3, an ECG signal is derived by way of a catheter 126 implanted in or about the heart, as in the right ventricle 128. This ECG signal is further developed at ECG circuitry 130, and synchronization pulses are in turn produced at a QRS synchronization circuit 132. As before, the "ready" signal from the inverter-capacitor circuit and the synchronization signal from the QRS synchronization circuit 132 are both fed to an AND gate 82. Upon coincidence of the "ready" and synchronization signals, AND gate 82 switches the discharge switch 84 to its conductive state, thereby discharging the storage and discharge capacitor 78 through the heart 76 by way of a catheter 72 implanted in or about the heart, as in the right atrium 74.

The operation of the circuit illustrated in FIG. 3 is as follows. When the knowledgeable patient experiences either atrial fibrillation, flutter or tachycardia, and elects to undergo cardioversion, he places the command magnet 112 at the appropriate location near the reed switch 114. The magnet pull closes the reed switch 114, clears the binary counter 124, and places the timer 116 in its counting state. After a preset delay, timer 116 produces a command which places switch 118 in its conductive state, and hence energy is delivered from the source 120 to the power inverter 52.

Once being cleared, binary counter 124 takes its first state which commands power inverter 52 to charge the discharge capacitor 78 to its lowest predetermined energy level. This is accomplished by the binary counter 124 developing an energy control signal, and feeding the same to the power inverter 52 along lines 50. In the same manner as explained above, when discharge capacitor 78 reaches the proper level of charging, a "ready" signal is issued and is passed to AND gate 82 via line 80. At the same time, the ventricular catheter 126 or another appropriate sensing lead senses the heart function, and a set of QRS synchronization pulses is produced by circuit 132 and fed to AND gate 82 via line 56.

Upon the simultaneous occurence of a "ready" signal and a QRS pulse, AND gate 82 switches discharge switch 84 to its conductive state and the discharge capacitor 78 discharges through the heart 76 of the patient via atrial catheter 72. Firing of capacitor 78 through the atrial catheter 72 issues a signal at line 134 which sets binary counter 124 to its second state. At the same time, the delay period of timer 116 is reinitiated to enable the patient to assess the effect of the first pulse.

If the patient successfully undergoes cardioversion, the command magnet 112 is removed, and the procedure is completed. If, however, after the elapse of the time delay set in timer 116, the patient determines that his heart is still in fibrillation, or undergoing flutter or tachycardia, another cardioversion will be attempted. With the inventive circuit, this second attempt is at a higher energy level.

After deciding that a second attempt at cardioversion is appropriate, the patient maintains command magnet 112 in its position opposite reed switch 114. As such, there is no "clear" signal issued to binary counter 124, and counter 124 remains in its second state after being advanced by the first discharge of the capacitor 78 through the heart. The preset delay in timer 116 elapses, and switch 118 is placed in its conductive state. Therefore, energy source 120 again energizes power inverter 52. Binary counter 124 then being in its second state, commands power inverter 52 to charge energy storage and discharge capacitor 78 to a higher level of energy. When capacitor 78 reaches this higher energy level, the capacitor is again discharged through the heart in proper synchronization with the QRS complex. This stepped discharge through the heart can be programmed, as desired, by presetting the number of stages of the binary counter 124.

It should be appreciated that as shown in the embodiment illustrated in FIG. 3, the QRS synchronization signal can be taken internally, as, for example, from a catheter implanted in the ventricle. Such an arrangement can also be used in the device of FIG. 1 in lieu of the external ECG console. Furthermore, while the specific embodiment of FIG. 3 employs a multi-stage discharge in increasing energy levels, such is not necessary in the basic design of the implantable device. Rather, the binary counter and associated circuitry can be eliminated, and the power inverter 52 set so that the first discharge through the heart is at a level sufficient to cardiovert the heart under most conditions of fibrillation, flutter or tachycardia. Furthermore, while synchronization with the QRS complex is believed to increase the safety factor involved in cardioverting a malfunctioning heart, cardioversion can be accomplished without synchronization. Under these conditions, the internal ventricular catheter and QRS circuitry could be eliminated.

While specific embodiments of the present invention have been described, it should be understood that these embodiments are described for purposes of illustration only. The foregoing description is not intended in any way to limit the scope of the present invention. Rather it is the intention that the scope of the invention be limited only as defined in the appended claims.

What is claimed is:

1. An implantable non-automatic cardioverting device for delivering cardioverting shocks to the heart of a wearer whose atrium requires cardioversion, said device being controlled directly by the wearer from external to the skin of the wearer, and comprising: storage means for storing an amount of energy for converting an abnormal supra-ventricular cardiac rhythm to normal sinus rhythm; delivery electrode means associating said storage means with the atrium of the wearer and for discharging the stored energy into the atrium; switch means for controlling the discharge of the stored energy into the atrium; charging means for delivering to said storage means said amount of energy for converting such abnormal supra-ventricular cardiac rhythm; receiver means for receiving commands from external to the skin of the wearer, for controlling the operation of said switch means, and for initiating the discharge of cardioverting energy into the atrium of the wearer in response to such commands; non-implantable portable actuating means for issuing said commands said actuating means being manually operated by said wearer upon said wearer's sensing of a condition requiring cardioversion of the atrium; command means for issuing a control signal for controlling the amount of energy which said charging means delivers to said storage means; means for limiting the amount of energy which said charging means delivers to said storage means in accordance with said control signal; means in said receiver means for receiving said control signals; comparator means for comparing a signal indicative of the amount of energy stored by said storage means with a signal representative of said control signal; and means for disabling said charging means once said storage means has stored the amount of energy indicated by said control signal.

2. The device of claim 1, and further comprising gate means for preventing the switch means for enabling the discharge of the stored energy into the atrium until the stored energy reaches the amount of energy indicated by said control signal.

3. The device of claim 1, wherein said control signal is a serial binary control word; and further comprising a control register for converting said serial binary control word into a parallel binary control word; and a digital-to-analog converter for converting said parallel binary control word into a corresponding analog signal, said analog signal being said signal representative of said control signal.

4. An implantable non-automatic cardioverting device for delivering cardioverting shocks to the heart of a wearer whose atrium requires cardioversion, said device being controlled directly by the wearer from external to the skin of the wearer, and comprising: storage means for storing an amount of energy for converting an abnormal supra-ventricular cardiac rhythm to normal sinus rhythm; delivery electrode means associating said storage means with the atrium of the wearer and for discharging the stored energy into the atrium; switch means for controlling the discharge of the stored energy into the atrium; charging means for delivering to said storage means said amount of energy for converting such abnormal supra-ventricular cardiac rhythm; receiver means for receiving commands from external to the skin of the wearer, for controlling the operation of said switch means, and for initiating the discharge of cardioverting energy into the atrium of the wearer in response to such commands; non-implantable portable actuating means for issuing said commands, said actuating means being manually operated by said wearer upon said wearer's sensing of a condition requiring cardioversion of the atrium; command means for issuing a control signal for controlling the amount of energy which said charging means delivers to said storage means; means for limiting the amount of energy which said charging means delivers to said storage means in accordance with said control signal; means in said receiver means for receiving said control signals; means for generating a timing signal at each appearance of the wearer's QRS complex; and gate means for preventing the switch means from enabling the discharge of the stored energy into the atrium except at a predetermined time relative to said QRS complex.

5. The device of claim 4, and further comprising means for sensing the wearer's QRS complex, said means for sensing including an implantable probe associating with wearer's heart.

6. The device of claim 4, wherein said gate means further prevents the switch means from enabling the discharge of the stored energy into the atrium until the stored energy reaches the amount of energy indicated by said control signal.

7. The device of claim 6, wherein said gate means is an AND gate for switching switch means to effect a discharge of stored energy into the atrium upon the simultaneous occurence of a signal indicating that said storage means is storing the amount of energy indicated by said control signal, and a timing signal.

8. A system for cardioverting a heart experiencing supra-ventricular cardiac rhythm, said system being controlled directly by the wearer and external to the skin of the wearer, and comprising: a cardioverting unit implanted beneath the skin of the wearer including a storage element for receiving and storing predetermined amounts of energy for converting an abnormal supra-ventricular cardiac rhythm to normal sinus rhythm, electrode means associated with said storage element and the heart of the wearer for delivering the stored energy to the atrium for converting the heart, switch means for enabling the discharge of the stored energy into the atrium upon storage by said storage means of said predetermined amounts of energy, charging means for delivering said predetermined amounts of energy to the storage element, means for disabling said charging means once said storage element has stored said predetermined amounts of energy, and a receiver for receiving commands from external to the skin of the wearer, for controlling the operation of said switch means and for initiating the discharge of the stored energy into the atrium in response to such commands; and a portable transmitter external to the skin of the wearer and operated by said wearer upon said wearer's sensing of a condition requiring cardioversion of the atrium, for transmitting command signals across the skin to said receiver for controlling the operation of said implanted cardioverting unit.

9. The device of claim 8, wherein said receiver means is a switch whose state is operable from external to the skin of the wearer to initiate operation of the atrial device.

10. The device of claim 9, and further comprising means for operating said switch which includes means for responding to a magnet located external to the skin of the wearer and aligned by said wearer with said switch.

11. The device of claim 9, and further comprising an implantable power source for providing the electrical power necessary for the operation of the implantable atrial device.

12. The device of claim 9, and further comprising a delay timer for delaying the discharge of the stored energy into the atrium for a predetermined period of time after said switch is operated from external to the skin of the wearer.

13. An implantable non-automatic cardioverting device for delivering cardioverting shocks to the heart of a wearer whose atrium requires cardioversion, said device being controlled directly by the wearer from external to the skin of the wearer, and comprising: storage means for storing an amount of energy for converting an abnormal supra-ventricular cardiac rhythm to normal sinus rhythm; delivery electrode means associating said storage means with the atrium of the wearer and for discharging the stored energy into the atrium; switch means for controlling the discharge of the stored energy into the atrium; charging means for delivering to said storage means said amount of energy for converting such abnormal supra-ventricular cardiac rhythm; receiver means for receiving commands from external to the skin of the wearer, for controlling the operation of said switch means, and for initiating the discharge of cardioverting energy into the atrium of the wearer in response to such commands; non-implantable portable actuating means for issuing said commands, said actuating means being manually operated by said wearer upon said wearer's sensing of a condition requiring cardioversion of the atrium; an implantable test load; implantable load switching means to alternatively associate said storage means with said delivery electrode means or said test load; and implantable means for sensing the operation of the implantable cardioverter when the stored energy is discharged into said test load and for verifying the operation of the device; and wherein said receiver means receives switching signals from external to the skin of the wearer which control the operation of said load switching means.

14. An implantable non-automatic cardioverting device for delivering cardioverting shocks to the heart of a wearer whose atrium requires cardioversion, said device being controlled directly by the wearer from external to the skin of the wearer, and comprising: storage means for storing an amount of energy for converting an abnormal supra-ventricular cardiac rhythm to normal sinus rhythm; delivery electrode means associating said storage means with the atrium of the wearer and for discharging the stored energy into the atrium; switch means for controlling the discharge of the stored energy into the atrium; charging means for delivering to said storage means said amount of energy for converting such abnormal supra-ventricular cardiac rhythm; receiver means for receiving amounts from external to the skin of the wearer, for controlling the operation of said switch means, and for initiating the discharge of cardioverting energy into the atrium of the wearer in response to such commands; non-implantable portable actuating means for issuing said commands, said actuating means being manually operated by said wearer upon said wearer's sensing of a condition requiring cardioversion of the atrium; wherein said receiver means is a switch whose state is operable from external to the skin of the wearer to initiate operation of the atrial device; and further comprising means for disabling said charging means once said storage means has stored said amount of energy for converting such supra-ventricular cardiac rhythm; and counter means for increasing the amount of energy stored by said storage means for successive discharges of the stored energy into the atrium of the wearer.

15. The device of claim 14, wherein said counter means is a multi-stage device for producing command signals determinative of the amount of energy which said charging means delivers to said storage means; and further comprising means for progressively increasing said amount of energy in successive stages of said counter means.

16. The device of claim 15, and further comprising means for advancing said counter means in stages for each discharge of said stored energy into the atrium.

17. The device of claim 16, and further comprising means for returning said counter means to its initial stage before each operation of said switch from external to the skin of the wearer.

18. The device of claim 15, and further comprising comparator means for comparing a signal indicative of the amount of energy stored by said storage means with a signal representative of the command signal produced by said counter means; and means for disabling said charging means once said storage means has stored the amount of energy determined by said command signal.

19. The device of claim 18, and further comprising gate means for preventing the switch from initiating the operation of the atrial device until the stored energy reaches the amount of energy determined by said command signal.

20. The device of claim 18, wherein the command signals are serial binary control words; and further comprising a control register for converting said serial binary control words into parallel binary control words; and a digital-to-analog converter for converting said parallel binary control words into corresponding analog signals, said analog signals being representative of the command signals issued by said counter means.

21. The device of claim 14, and further comprising a delay timer for separating successive discharges of stored energy into the atrium by a predetermined period of time.

22. An implantable non-automatic cardioverting device for delivering cardioverting shocks to the heart of a wearer whose atrium requires cardioversion, said device being controlled directly by the wearer from external to the skin of the wearer, and comprising: storage means for storing an amount of energy for converting an abnormal supra-ventricular cardiac rhythm to normal sinus rhythm; delivery electrode means associating said storage means with the atrium of the wearer and for discharging the stored energy into the atrium; switch means for controlling the discharge of the stored energy into the atrium; charging means for delivering to said storage means said amount of energy for converting such abnormal supra-ventricular cardiac rhythm; receiver means for receiving commands from external to the skin of the wearer, for controlling the operation of said switch means, and for initiating the discharge of cardioverting energy into the atrium of the wearer in response to such commands; non-implantable portable actuating means for issuing said commands, said actuating means being manually operated by said wearer upon said wearer's sensing of a condition requiring cardioversion of the atrium; wherein said receiver means is a switch whose state is operable from external to the skin of the wearer to initiate operation of the atrial device; and further comprising means for generating a timing signal at each appearance of the wearer's QRS complex; and gate means for preventing the switch means from enabling the discharge of the stored energy into the atrium except at a predetermined time relative to said QRS complex.

23. The device of claim 22, and further comprising means for sensing the wearer's QRS complex by way of an implantable probe associating with the wearer's heart.

24. The device of claim 22, wherein said gate means further prevents the switch means from enabling the discharge of the stored energy into the atrium until the stored energy reaches said amount of energy for converting such abnormal supra-ventricular rhythm.

25. The device of claim 24, wherein said gate means is an AND gate for operating said switch means to effect a discharge of stored energy into the atrium upon the simultaneous occurrence of said storage means storing said amount of energy for converting such abnormal supra-ventricular cardiac rhythm, and a timing signal.

26. An implantable cardioverting device for converting an abnormal cardiac rhythm to normal sinus rhythm, the device comprising: storage means for storing an amount of energy for converting an abnormal cardiac rhythm to normal sinus rhythm; charging means for delivering to said storage means said amount of energy; delivery electrode means associating said storage means with the heart of the wearer and for discharging the stored energy into the heart; an implantable test load associated with said storage means for receiving the stored energy therefrom; implantable load switching means to alternately associate said storage means with said delivery electrode means or said test load; implantable means for sensing the operation of the implantable device when the stored energy is discharged into said test load for verifying the operation of the device; and non-implantable control means for controlling the operation of said load switching means.

27. The device recited in claim 26, and further comprising implantable receiver means for receiving commands from said non-implantable control means, for initiating the discharge of cardioverting energy into the heart of the wearer in response to such commands.

28. The device recited in claim 26, and further comprising receiver means for receiving commands from said non-implantable control means, for operating said load switching means, and for thereby controlling the discharge of stored energy into said test load or into the heart of the wearer.

29. The device recited in claim 26, wherein said delivery electrode means associates with the atrium of the wearer, and wherein said abnormal cardiac rhythm is abnormal supra-ventricular cardiac rhythm.

30. The device recited in claim 26, wherein said means for monitoring includes implantable transmitter means to transmit signals across the skin of the wearer; and non-implantable receiver means for receiving the signals transmitted by said transmitter means.

* * * * *